(12) United States Patent
Sakai et al.

(10) Patent No.: US 10,365,287 B2
(45) Date of Patent: Jul. 30, 2019

(54) METHOD FOR DETERMINING BIOPOLYMER USING NANOPORE, AND SYSTEM AND KIT THEREFOR

(75) Inventors: Tomoyuki Sakai, Kokubunji (JP); Takeshi Fujita, Niiza (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 442 days.

(21) Appl. No.: 13/148,479

(22) PCT Filed: Mar. 1, 2010

(86) PCT No.: PCT/JP2010/001352
§ 371 (c)(1),
(2), (4) Date: Aug. 9, 2011

(87) PCT Pub. No.: WO2010/116595
PCT Pub. Date: Oct. 14, 2010

(65) Prior Publication Data
US 2011/0308950 A1    Dec. 22, 2011

(30) Foreign Application Priority Data

Mar. 30, 2009    (JP) ................................ 2009-080867

(51) Int. Cl.
*G01N 33/68*    (2006.01)
*G01N 33/487*    (2006.01)

(52) U.S. Cl.
CPC ... *G01N 33/6803* (2013.01); *G01N 33/48721* (2013.01)

(58) Field of Classification Search
CPC ......... G01N 33/48721; G01N 33/6803; G01N 27/3278; C12Q 2565/629; C12Q 2565/631
USPC ............... 204/403.01–403.15; 205/778, 792; 435/6.1, 6.12
See application file for complete search history.

(56) References Cited

U.S. PATENT DOCUMENTS

| | | | |
|---|---|---|---|
| 5,795,782 A | * | 8/1998 | Church et al. ..................... 436/2 |
| 6,627,067 B1 | * | 9/2003 | Branton ................ B24B 37/013 |
| | | | 204/403.06 |
| 6,627,076 B2 | | 9/2003 | Griffiths |
| 2003/0143614 A1 | * | 7/2003 | Drmanac .......................... 435/6 |

(Continued)

FOREIGN PATENT DOCUMENTS

| | | |
|---|---|---|
| JP | 2004-233356 | 8/2004 |
| JP | 2005-524413 | 8/2005 |

(Continued)

OTHER PUBLICATIONS

John J. Kasianowicz et al., Characterization of individual polynucleotide molecules using a membrane channel, Proc. Natl. Acad. Sci. USA, Nov. 1996, pp. 13770-13773, vol. 93.

(Continued)

*Primary Examiner* — Maris R Kessel
(74) *Attorney, Agent, or Firm* — Baker Botts L.L.P.

(57) ABSTRACT

Although analysis can be very quickly conducted at a low cost by a method for measuring a biopolymer using a nanopore, the accuracy of distinguishing the individual monopolymers constituting the biopolymer is low. To both ends of a biopolymer through a nanopore, molecules which are larger than the nanopore are attached and then the biopolymer is reciprocated by an external force to thereby perform repeated measurements.

13 Claims, 14 Drawing Sheets

(56) References Cited

U.S. PATENT DOCUMENTS

| | | |
|---|---|---|
| 2005/0026304 A1* | 2/2005 | Bruhn et al. .................. 436/518 |
| 2006/0057585 A1* | 3/2006 | McAllister ........................ 435/6 |
| 2007/0042366 A1 | 2/2007 | Ling |
| 2007/0190542 A1 | 8/2007 | Ling et al. |
| 2007/0190543 A1* | 8/2007 | Livak ................ 435/6 |
| 2007/0231795 A1 | 10/2007 | Su |
| 2009/0023146 A1* | 1/2009 | Harnack et al. .................. 435/6 |
| 2009/0136958 A1* | 5/2009 | Gershow .............. C12Q 1/6825 435/6.13 |
| 2010/0331194 A1* | 12/2010 | Turner ................ C12Q 1/6869 506/2 |

FOREIGN PATENT DOCUMENTS

| | | |
|---|---|---|
| JP | 2006-078491 | 3/2006 |
| JP | 2006-113057 | 4/2006 |
| JP | 2006-119140 | 5/2006 |
| JP | 2006-284231 | 10/2006 |
| JP | 2006-526777 | 11/2006 |
| JP | 2008-524600 | 7/2008 |
| WO | WO 03/106620 | 12/2003 |
| WO | WO 2004/085609 | 10/2004 |
| WO | WO 2008/005674 A2 | 1/2008 |

OTHER PUBLICATIONS

Jiali Li et al., Ion-beam sculpting at nanometer length scales, Nature, Jul. 12, 2001, pp. 166-169, vol. 412. www.nature.com.

Michael Zwolak, electronic Signature of DNA Nucleotides via Transverse Transport, Nano Letters, 2005, pp. 421-424, vol. 5, No. 3.

Scott L. Cockroft et al., A single-Molecule Nanopore Device Detects DNA Polymerase Activity with Single-Nucleotide resolution, J. American Chemical Society, 2008, pp. 818-820, vol. 130, No. 3.

Marc Gershow et al., recapturing and trapping single molecules with a solid-state nanopore, Nature nanotechnology, Dec. 2007, pp. 775-779, vol. 2. www.nature.com/naturenaotechnolgy.

JP Office Action Appln. No. 2009-080867 dated Jun. 4, 2013.

* cited by examiner

MIGRATING DIRECTION

WAVELENGTH DIRECTION

METHOD FOR DETERMINING BIOPOLYMER USING NANOPORE, AND SYSTEM AND KIT THEREFOR

TECHNICAL FIELD

The present invention relates to a technical field concerning a structure and method for performing high-precision measurement and analysis on a biopolymer such as a DNA, RNA, or protein using a nanopore structure.

BACKGROUND ART

For diagnosis of diseases or drug discovery, it is important to analyze a biopolymer such as a nucleic acid (DNA or RNA) or a protein. In particular, since a DNA is the key substance of life, analysis thereof, that is, determination of a base sequence is quite significant to the above object. As for a principal method for analyzing the base sequence of a DNA, primarily, chemical or enzymatic reaction is utilized in order to produce a group of DNA fragments of various lengths, which have a predetermined terminal base species, with respect to a mold DNA whose sequence is wanted to be determined. The DNA fragment group is produced for each of four base species. Thereafter, gel electrophoresis is used to separate each of the DNA fragment groups in order of a molecular weight. The DNA fragment groups are introduced into a separation medium and a voltage is applied. Since a DNA fragment is a polyelectrolyte having a negative charge as a whole, electrophoresis is made in a negative-to-positive direction. In a gel, since a longer DNA fragment exhibits a smaller mobility, even DNA fragments having a difference of only one base length between them can be separated from each other. After the separation is completed, when the lengths of DNA fragments dependent on the terminal base species are measured, the positions of the base species in the mold DNA are found. Through the foregoing manipulations, the base sequence of the mold DNA is determined. In the above method, production of the DNA fragment groups or work of electrophoresis is quite labor-intensive, and an analysis time is long. Besides, a running cost is high.

Patent literature 1 and non-patent literature 1 describe a biopolymer analysis method using a microscopic pore of several nanometers in diameter formed on a thin membrane of a lipid bilayer, which is an insulating membrane, using alpha-hemolysin, that is, a nanopore. A thin membrane having the nanopore is interposed between two solution vessels, a voltage gradient is brought about between the solution vessels, and a current is measured. When a DNA molecule that is a biopolymer is put in one of the solution vessels, the DNA molecule passes through the nanopore due to the voltage gradient, and thus moves to the other solution vessel. When the DNA molecule passes through the nanopore, the DNA molecule blocks a flow of ions in the nanopore. This brings about a decrease in a current (blockage current). By measuring the magnitude of the blockage current and the duration of the blockage current, the length of an individual DNA molecule passing through the nanopore can be detected. In addition, the species of individual bases constituting the DNA molecule can be theoretically distinguished from one another.

In patent literature 2 and non-patent literature 2, instead of the nanopore formed in a lipid bilayer using alpha-hemolysin, a nanopore is formed in a silicon nitride ($Si_3N_4$) membrane, which is an insulating membrane, using a technology referred to as ion-beam sculpting. A blockage current of a single-stranded DNA molecule is then measured.

In non-patent literature 3, a proposal is made of means other than the foregoing blockage current as a method for measuring a DNA molecule that passes through a nanopore. A pair of metallic electrodes is disposed on the internal surface of the nanopore, and a tunneling current occurring when a DNA strand passes between the metallic electrodes is measured. Even in this method, as long as the size of the electrodes or the like is appropriately controlled, species of individual bases constituting the DNA molecule that passes through the nanopore can be distinguished from one another.

Patent literature 3 describes a method for determining a base sequence of a target DNA through hybridization of a known-sequence probe to a target single-stranded DNA and detection of a position of hybridization of the known-sequence probe using a nanopore. A known-sequence probe is hybridized to a target single-stranded DNA molecule that should be determined, and the DNA molecule having undergone the hybridization is passed through a nanopore. Since a blockage current differs between a single-stranded site and a double-stranded site of the DNA molecule, when the DNA molecule passes through the nanopore, if the current is measured, the position of hybridization of the known-sequence probe can be identified. Plural kinds of known-sequence probes having different sequences are used to perform the foregoing manipulations, and data items of the positions of hybridization of the known-sequence probes to the target DNA molecule are acquired. The acquired data items are converted into sequence data using a computer algorithm. Thus, the sequence of the target DNA molecule can be determined.

Non-patent literature 4 describes a consequence that when the positive and negative polarities of an applied voltage are reversed immediately after a DNA molecule passes through a nanopore, the same DNA molecule passes through the same nanopore again.

In non-patent literature 5, elongation reaction of a DNA molecule is induced in a nanopore, and presence or absence of the elongation reaction is verified by measuring a blockage current.

CITATION LIST

Patent Literature

Patent literature 1: U.S. Pat. No. 5,795,782
Patent literature 2: U.S. Pat. No. 6,627,076
Patent literature 3: U.S. Patent Publication No. 2007/0190542

Non-Patent Literature

Non-patent literature 1: PNAS 1996, Vol. 93, pp. 13770-13773
Non-patent literature 2: Nature 2001, Vol. 412, pp. 166-169
Non-patent literature 3: NANO Letters 2005, Vol. 5, pp. 421-424
Non-patent literature 4: Nature Nanotechnology 2007, Vol. 2, pp. 775-779
Non-patent literature 5: JACS 2008, Vol. 130, pp. 818-820

SUMMARY OF INVENTION

Technical Problem

As for determination of a sequence of a biopolymer, or more particularly, a DNA molecule using electrophoresis, an analysis time is long and a running cost is high. In contrast, determination of the sequence of the DNA molecule using a nanopore which is described in patent literature 1 or non-patent literature 3 has a potential of fast and inexpensive analysis but is confronted with problems described below.

In patent literature 1, a difference in a blockage current, which occurs when a DNA molecule passes through a nanopore and depends on a base species, is so minute that it is hard to distinguish one base species from another. Therefore, precision in the distinction is very low. In order to improve the precision in the distinction, it is necessary to set the membranous thickness near the nanopore to a value equivalent to about one base, that is, a sub-nanometer. However, it is hard for an existing technology to attain the membranous thickness.

In non-patent literature 3, the magnitude of a tunneling current occurring when a DNA molecule passes through a nanopore depends on, aside from a base species passing through the nanopore, orientation near electrodes used to measure the tunneling current of the base. Currently, it is hard to control the orientation of a passing nucleic acid. Therefore, repetitive measurement is needed in order to upgrade the precision in base species separation.

By the way, according to the method described in patent literature 3, since a position of hybridization of a known-sequence probe to a target DNA molecule is detected, it is unnecessary to distinguish bases species from one another. However, it is necessary to highly precisely detect a position of hybridization on a single base level. In addition, it is necessary to hybridize plural different kinds of known-sequence probes to the same target DNA molecule in different places or at different timings and to detect the positions. Specifically, the target DNA molecule has to be amplified and introduced into different solutions in which the different known-sequence probes exist. The target DNA molecule and known-sequence probes have to be hybridized to one another. Using different nanopores or using the same nanopore at different timings, measurement has to be performed. Otherwise, after the target DNA molecule hybridized to a certain known-sequence probe is measured using the nanopore, the target DNA molecule is sampled, denatured, and returned to a single strand. The single-stranded DNA is then hybridized to a different known-sequence probe, and measured again using the nanopore. This procedure has to be repeated. In either case, quite labor-intensive work is needed.

As described in non-patent literature 4, when applying a reverse voltage after a DNA molecule passes through a nanopore is repeated, the same DNA molecule can be measured plural times using the same nanopore. Therefore, although there is a possibility that measurement precision may be improved owing to repetitive measurement, application of a voltage through high-precision feedback is needed. In addition, if plural kinds of DNA molecules coexist, there is a fear of contamination. Further, the directions of the DNA molecules get randomized.

In non-patent literature 5, polyethylene glycol (PEG)-biotin-mediated streptavidin is bound to a 5' end of a target DNA molecule, and a DNA primer including several bases is hybridized to a 3'-end side thereof. The 3' end of the target DNA molecule is thus double-stranded, and the target DNA molecule is reciprocated through a nanopore. Due to repetitive measurement using the reciprocation, there arises a possibility that high-precision nanopore measurement can be achieved. However, it is hard to control the position of hybridization of a DNA probe to the target DNA molecule. The DNA probe may be bound to various positions in the target DNA molecule, and the reciprocation may not be achieved. In addition, since the diameter of a double-stranded DNA is on the order of 2 nm, if the diameter of the nanopore is equal to or larger than 2 nm, the double-stranded part passes through the nanopore. The reciprocation becomes hard to do.

Solution to Problem

The present invention provides a method, system, and kit making it possible to stably achieve repetitive measurement for improvement of measurement precision in nanopore measurement of a biopolymer molecule such as a nucleic acid or protein.

A first solution vessel and a second solution vessel are included, and the solution vessels are partitioned by a thin membrane. The thin membrane has a pore of a nanometer size, that is, a nanopore formed therein. A molecule (first stopper molecule) having a larger size than the diameter of the aperture of the nanopore is bound to one of the ends of a biopolymer molecule, and the resultant biopolymer molecule is introduced into the first solution vessel. By applying an external force, the biopolymer is driven to pass through the nanopore, and thus moved to the second solution vessel. Using the first stopper molecule, the biopolymer molecule passing through the nanopore ceases moving halfway. After the movement of the biopolymer molecule is ceased, a molecule (second stopper molecule) that is larger than the diameter of the aperture of the nanopore and exists in the second solution vessel is bound to the other end of the biopolymer molecule. Thereafter, while the biopolymer molecule is reciprocated between the solution vessels by applying an external force, measurement is carried out in order to identify the biopolymer molecule.

Binding the second stopper molecule to the biopolymer molecule may be performed while the biopolymer molecule is moving through the nanopore. When the second stopper molecule is bound to the biopolymer molecule, the external force for driving the biopolymer molecule may be stopped or may be kept applied. The second stopper molecule may be preliminarily put in the second solution vessel, or may be introduced thereinto after one end of the biopolymer molecule is moved to the second solution vessel. The stopper molecules may be the same molecule or different molecules. As means for driving the biopolymer, if the biopolymer molecule has charge, a voltage gradient may be brought about between the solution vessels, or an electrochemical gradient may be brought about by differentiating an ion composition between the solution vessels. Otherwise, a flow of a solution may be produced for driving. As means for measurement, a value of a current (blockage current) flowing through the nanopore between the solution vessels will do, or a value of a current (tunneling current) flowing between electrodes disposed in the nanopore will do. The biopolymer molecule may be labeled with a fluorescent substance, and excited near the nanopore in order to detect the emitted fluorescent light. With the stopper molecules bound to both the ends of the biopolymer molecule, a certain substance may be bound to or separated from the biopolymer molecule. For example, as described in non-patent literature 3, when a DNA molecule sequence is determined on a hybridization basis, measurement can be readily and highly precisely achieved using the aforesaid method. A stopper molecule is bound to both the ends of a DNA molecule, and a known-sequence probe is introduced into a solution vessel and hybridized to a target DNA molecule. The target DNA molecule is reciprocated between the solution vessels, and the position of hybridization is detected through blockage current measurement. Thereafter, the known-sequence probe is separated from the target DNA molecule through denaturing manipulations, and another known-sequence probe is used to repeat the same manipulations as the foregoing ones. Owing to the means, different known-sequence probes can be readily hybridized to the same target DNA molecule whatever number of times. In addition, since repetitive measurement can be performed, the position of hybridization can be highly precisely measured.

A method for determining a biopolymer in accordance with the present invention is a method for determining the alignment of monomers constituting a biopolymer that is an object of measurement, using an apparatus including a first solution vessel, a second solution vessel, and a thin membrane which partitions the first solution vessel and second solution vessel and has a nanopore. The method is characterized by a step of introducing the biopolymer, which has a first molecule, which is larger than the nanopore, bound to one end thereof, into the first solution vessel, a step of moving the biopolymer from the first solution vessel to the second solution vessel through the nanopore, a step of introducing a second molecule, which is larger than the nanopore, into the second solution vessel, and binding the molecule to the other end of the biopolymer, a step of moving the biopolymer between the first solution vessel and second solution vessel through the nanopore, and measuring a temporal change in a signal generated along with the movement of the biopolymer, calculating the signal as data dependent on the species of monomers constituting the biopolymer, and determining the alignment of the monomers constituting the biopolymer.

A system for determining a biopolymer in accordance with the present invention is a system that uses an apparatus, which includes a thin membrane having a nanopore, to introduce a molecule that is larger than the size of the nanopore and is bound to a biopolymer that is an object of measurement. The apparatus includes first and second solution vessels that are partitioned by the thin membrane, driving means that moves the biopolymer between the first solution vessel and second solution vessel through the nanopore, means that introduces the biopolymer, which has the molecule bound to one end of the biopolymer that is the object of measurement, into the first solution vessel, means that introduces the molecule, which is bound to the other end of the biopolymer having passed through the nanopore, into the second solution vessel, detecting means that detects a signal generated along with the movement of the biopolymer made by the driving means, and calculating means that measures a temporal change in the signal detected by the detecting means, calculates the signal as data dependent on the species of monomers constituting the biopolymer, and determines the alignment of the monomers constituting the biopolymer.

A kit for determining a biopolymer in accordance with the present invention is a kit including an apparatus that includes a thin membrane having a nanopore, and a molecule which is larger than the size of the nanopore and is bound to a biopolymer that is an object of measurement. The apparatus includes first and second solution vessels partitioned by the thin membrane, driving means that moves the biopolymer through the nanopore between the first solution vessel and second solution vessel, means that introduces the biopolymer, which has the molecule bound to one end of the biopolymer that is the object of measurement, into the first solution vessel, means that introduces the molecule, which is bound to the other end of the biopolymer having passed through the nanopore, into the second solution vessel, detecting means that detects a signal generated along with the movement of the biopolymer made by the driving means, and calculating means that measures a temporal change in the signal detected by the detecting means, calculates the signal as data dependent on the species of monomers constituting the biopolymer, and determines the alignment of the monomers constituting the biopolymer. The molecule is streptavidin or a bead to be bound to the biopolymer by a DIG-anti-DIG antibody bond.

Advantageous Effects of Invention

The present invention permits stabilized repetitive measurement of a biopolymer molecule using a nanopore, and enables inexpensive, fast, and high-precision measurement.

DESCRIPTION OF EMBODIMENTS

Figure 1A:
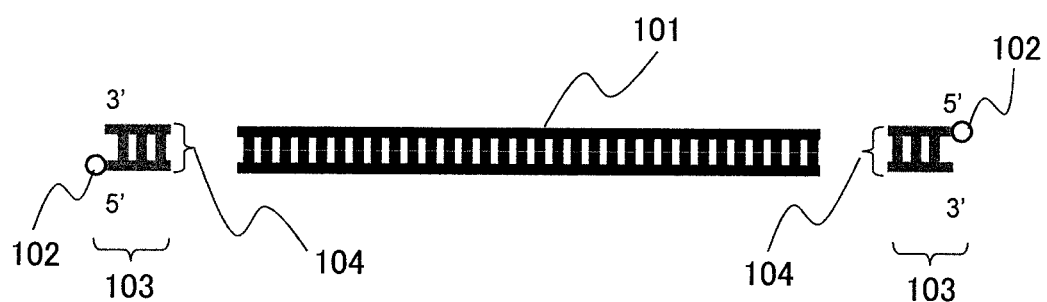
FIG. 1A and FIG. 1B include illustrative diagrams of the inside of a sample solution during sample preprocessing.

Referring to the drawings, embodiments of the present invention will be described below.

Embodiment 1

Figure 1B:
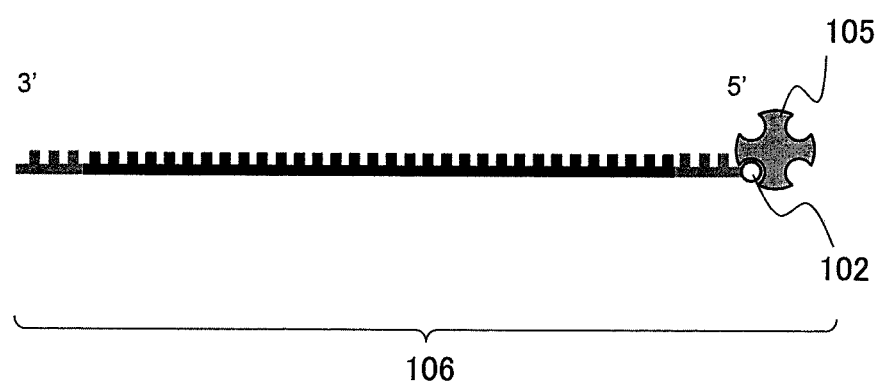
Figure 2A:
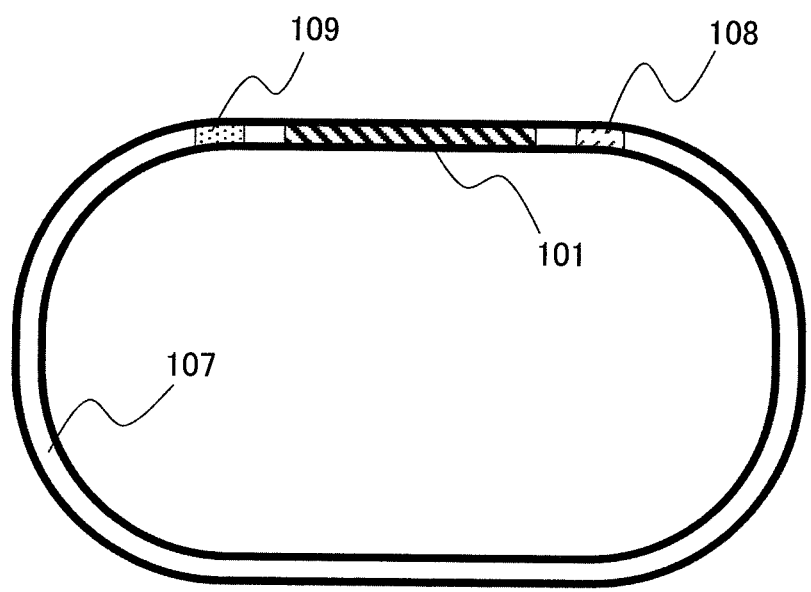
FIG. 2A and FIG. 2B include illustrative diagrams of a sample preprocessing method utilizing a vector.
Figure 2B:
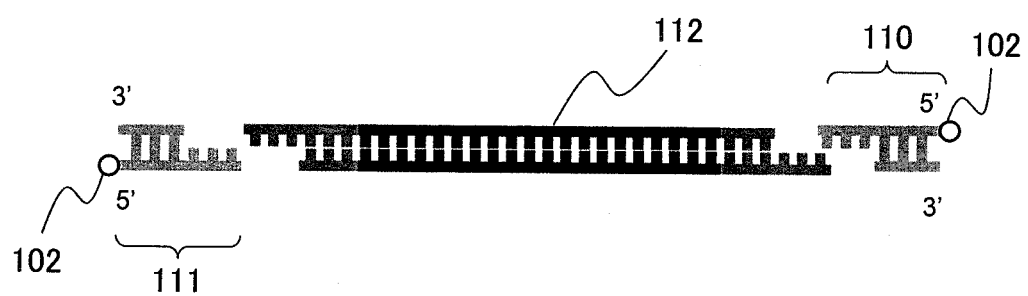

A description will be made of a method for determining a base sequence of a DNA molecule through measurement of a tunneling current in a nanopore using the present invention. FIGS. 1A and 1B illustratively show a state of the inside of a sample solution during sample preprocessing preceding measurement. In the solution, a target DNA molecule 101 that is double-stranded, and a double-stranded synthetic probe 103 having a 5' end thereof labeled with biotin 102 coexist. An end face 104 of the double-stranded synthetic probe 103 that is not labeled with biotin has undergone blunt-ending reaction. Using S1 nuclease or the like, blunt-ending reaction is performed on both the ends of the target DNA molecule 101. After the blunt-ending reaction is performed on both the ends of the target DNA molecule 101, a ligase is used to ligate the synthetic probe 103 to both the ends of the target DNA molecule 101. After the ligation reaction is terminated, a sample is separated in size through acrylamide gel electrophoresis. Only the target DNA molecule 101 having the synthetic probe 103 bound to both the ends thereof is cut out of an acrylamide gel and eluted to distilled water. Through the above manipulations, the synthetic probes 103 that are ligated to each other and the target DNA molecules 101 that are ligated to each other can be excluded. Thereafter, a buffer solution containing streptavidin 105 is mixed in the solution into which the target DNA molecule 101 having the synthetic probe bound to both the ends thereof is eluted. The biotin 102 with which the 5' end of target DNA molecule 101 is labeled is bound to the streptavidin 105, and a DNA is denatured by applying heat. Thus, a DNA fragment 106 containing the target DNA molecule 101 having streptavidin bound to the 5' end thereof as shown in FIG. 1B is produced. FIGS. 2A and 2B illustratively show another method for producing the DNA fragment 106. The target DNA molecule 101 is inserted to part of a multi-cloning site in a vector 107. Thereafter, the target DNA molecule 101 is cut at restriction sites 108 and 109 in the vector through restriction enzyme digestion so that the target DNA molecule 101 can be sandwiched. A double-stranded synthetic probe 110 including the nick end of the restriction site 108 and having a 5' end thereof labeled with biotin 102 and a double-stranded synthetic probe 111 including the nick end of the restriction site 109 and having a 5' end thereof labeled with the biotin 102 are introduced into a fragment 112 cut from the vector. A ligation is then carried out. Thereafter, the biotin 102 with which the 5' end is labeled and streptavidin 105 are bound to each other, and the DNA is denatured by applying heat. Eventually, a DNA fragment 106 containing the target DNA molecule 101 that has streptavidin bound to the 5' end thereof as shown in FIG. 1B is produced.

Figure 3:
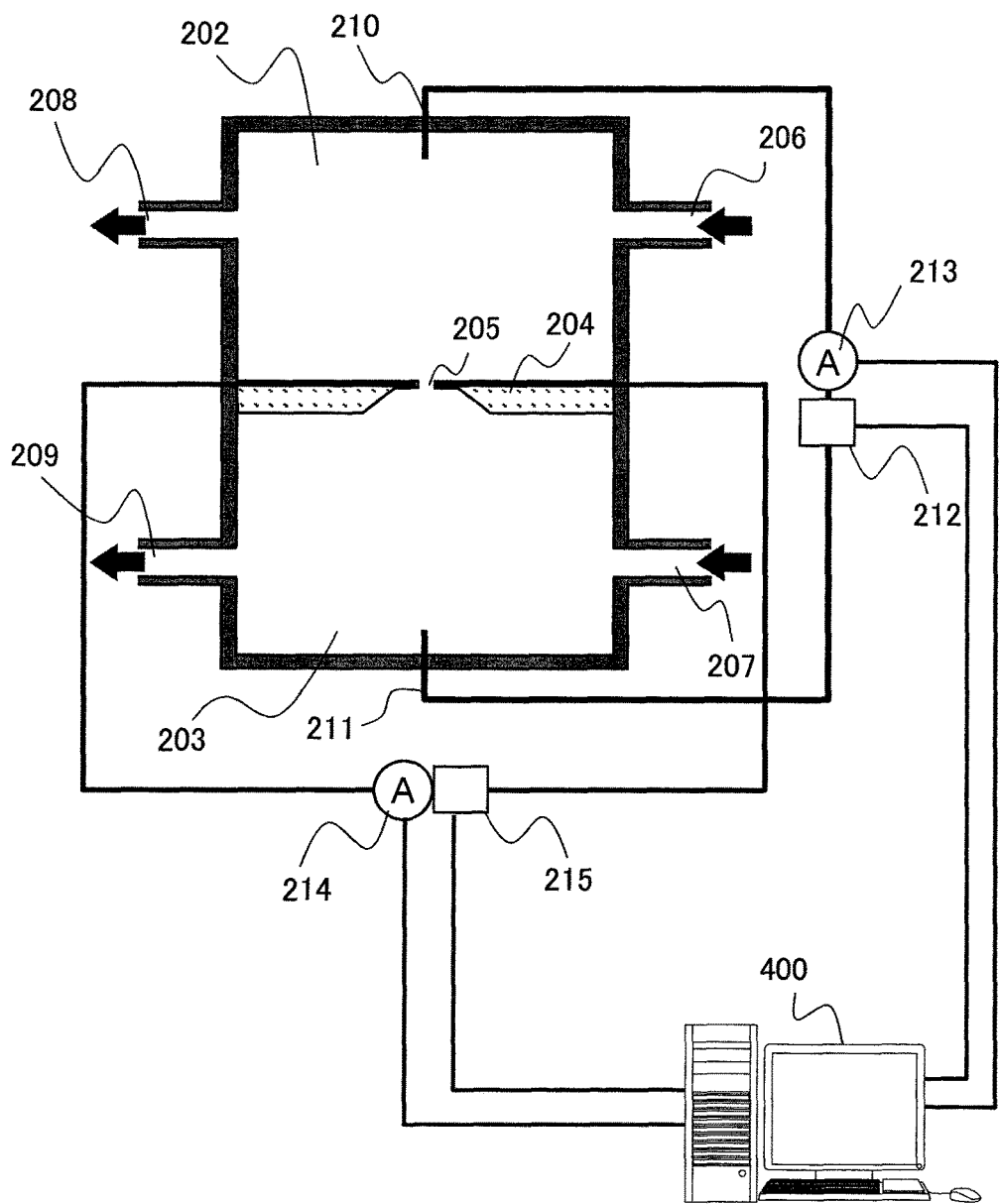
FIG. 3 is a schematic diagram of a nanopore apparatus employed in an embodiment 1.

FIG. 3 is a schematic diagram of a nanopore apparatus employed in the present embodiment. The nanopore apparatus includes a first solution vessel 202, a second solution vessel 203, and a nanopore thin membrane 204 that separates the solution vessels from each other. The solution vessels are provided with introduction ports 206 and 207 respectively through which a solution is introduced, and discharge ports 208 and 209 respectively through which the solution is discharged. In order to bring about a voltage gradient between the solution vessels via the nanopore thin membrane 204, the solution vessels 202 and 203 are provided with electrodes 210 and 211 respectively. The electrodes 210 and 211 are connected to a voltage source 212 capable of changing polarities and an ammeter 213. The nanopore thin membrane 204 is formed with a thin membrane of an insulator having a nanopore 205 of 1 nm in diameter formed therein. Herein, $Si_3N_4$ is adopted as the material of the insulator thin membrane. Alternatively, a plastic material such as $SiO_2$ or asphaltene will do. Further, a thin membrane produced by coating an insulating material over the surface of a metallic membrane made of Al or the like. Herein, the diameter of the nanopore 205 is 1 nm. Alternatively, the diameter may range about 0.5 nm to about 50 nm. Incidentally, the size of streptavidin used as a stopper molecule is on the order of 5 nm and much larger than the size of the nanopore. As the size of the stopper molecule relative to the diameter of the nanopore, any size capable of hindering advancement of a DNA fragment will do. For improvement of precision, the size is preferably 1.2 times to 50 times larger.

Figure 4A:
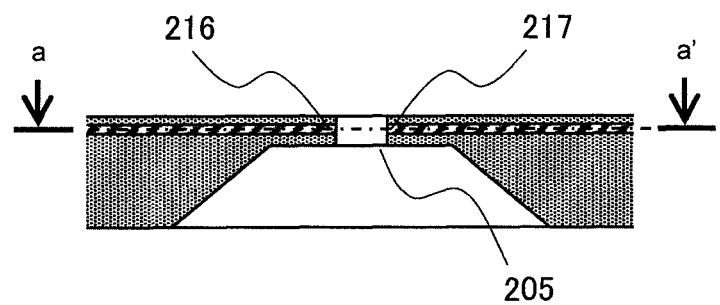
FIG. 4A and FIG. 4B include enlarged diagrams of the vicinity of a nanopore in the embodiment 1.
Figure 4B:
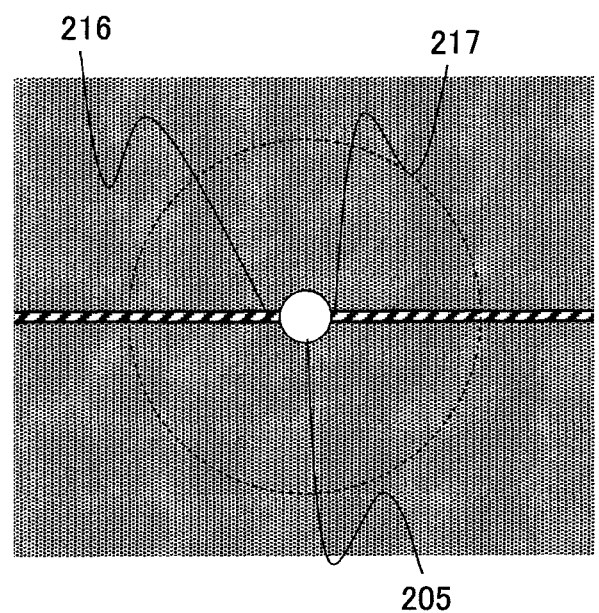

FIG. 4A is an enlarged view of the vicinity of the nanopore 205. FIG. 4B is an a-a' sectional view of FIG. 4A. A pair of electrodes 216 and 217 is disposed on the internal surface of the nanopore 205. The electrodes 216 and 217 are connected to a voltage source 215 and an ammeter 214.

Figure 5:
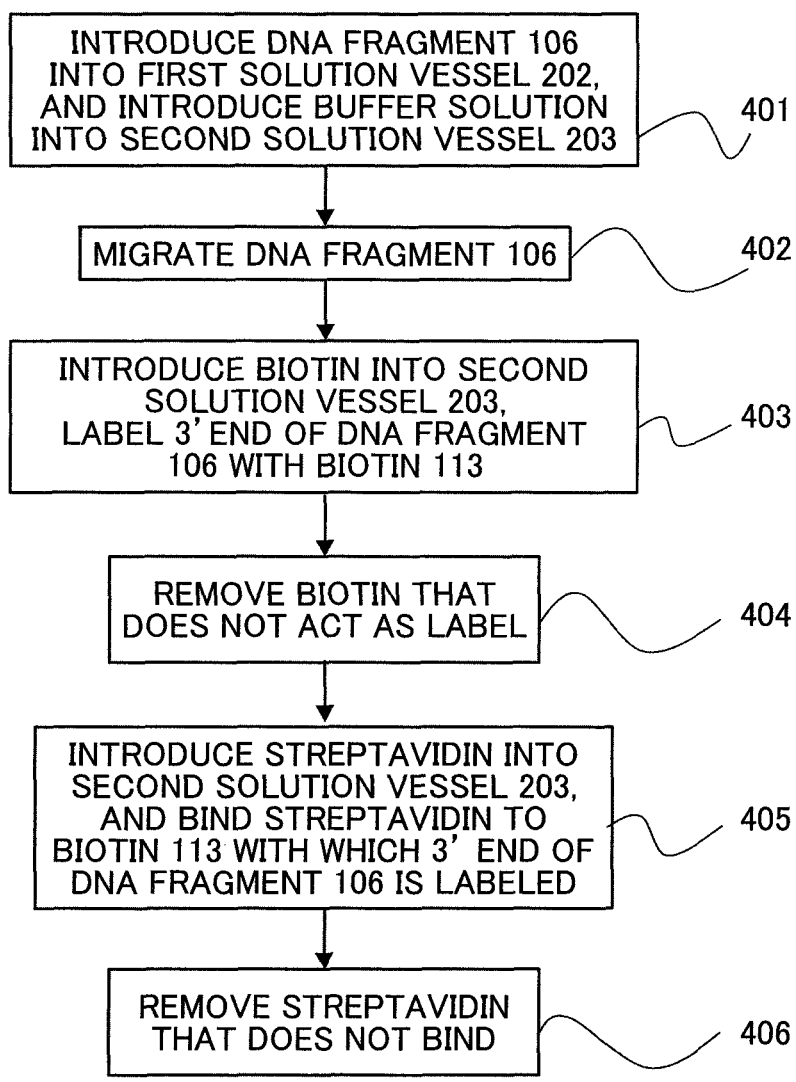
FIG. 5 is a flowchart of binding streptavidin to a 3' end of a DNA fragment.

Referring to the flowchart of FIG. 5, a description will be made of a method for binding streptavidin to the 3' end of the DNA fragment 106. Incidentally, FIG. 6 illustratively shows a procedure of binding streptavidin to the 3' end of the DNA fragment 106.

Figure 6A:
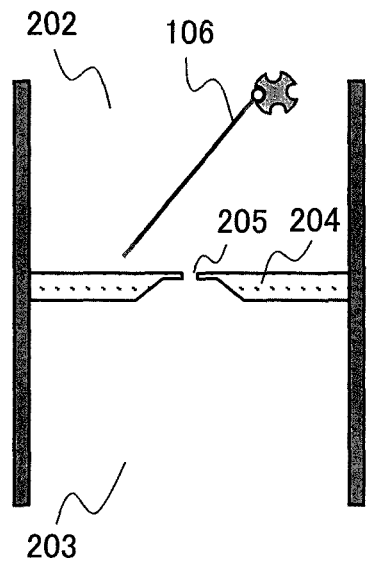
FIG. 6A-FIG. 6D include illustrative diagrams of a situation where streptavidin is bound to the 3' end of the DNA fragment.
Figure 6B:
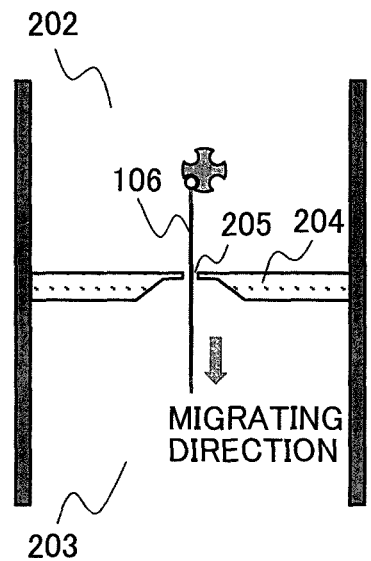
Figure 6C:
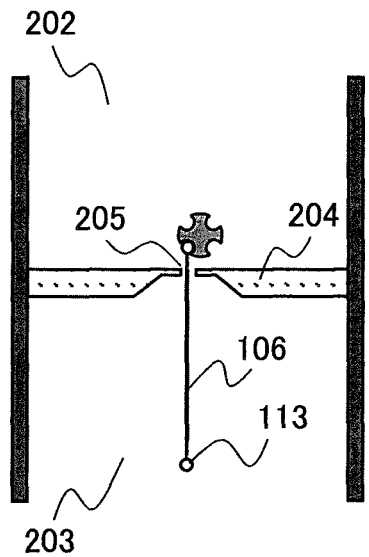

To begin with, the DNA fragment 106 obtained with the foregoing method is mixed in a buffer solution, and introduced into the first solution vessel 202 through the introduction port 206, and the buffer solution alone is introduced into the second solution vessel 203 through the introduction port 207 (401) (FIG. 6A). A voltage is applied from the voltage source 212 so that the electrode 210 can behave as a cathode and the electrode 211 can behave as an anode. This causes the DNA fragment 106 to migrate from the first solution vessel 202 to the second solution vessel 203 (402) (FIG. 6B). Concurrently with the voltage application, the ammeter 213 is used to measure a flow of ions through the nanopore 205. Since the size of streptavidin 105 is on the order of 5 nm, the streptavidin cannot pass through the nanopore of 1 nm in diameter. The DNA fragment 106 has therefore the 3' end (end that is not labeled by the streptavidin 105) thereof first introduced into the nanopore 205. When the DNA fragment 106 is introduced into the nanopore 205, a current value decreases. As mentioned previously, the size of the streptavidin 105 is larger than the diameter of the nanopore 205. Therefore, immediately before the streptavidin 105 passes through the nanopore 205, the movement of the DNA fragment 106 to the second solution vessel 203 is ceased. After the decrease in a current is verified, a biotin-3' end-DNA-labeling kit is inserted to the second solution vessel 203 through the introduction port 207 in order to labeled the 3' end of the DNA fragment 106 with biotin 113 (403) (FIG. 6C).

Figure 6D:
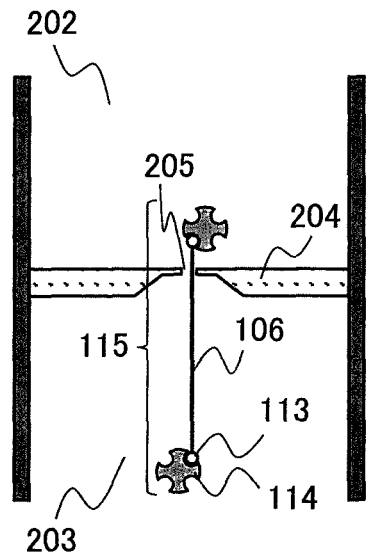

After biotin labeling is completed, the buffer alone is introduced through the introduction port 207 in order to remove biotin, which has not reacted, from the second solution vessel 203 (404). Thereafter, a solution containing streptavidin is introduced through the introduction port 207 so that the streptavidin 114 can be bound to the biotin 113 with which the 3' end of the DNA fragment 106 is labeled. Thus, an arrayed DNA fragment 115 is produced (405) (FIG. 6D). The buffer alone is introduced through the introduction port 207 in order to remove streptavidin, which has not reacted, from the second solution vessel 203 (406).

As described above, streptavidin that is one and the same substance is used as the first and second stopper molecules. Alternatively, different substances may be used. For example, as another method for producing the arrayed DNA fragment 115 using different substances as the first and second stopper molecules, a method to be described below is available. In the method shown in FIG. 2, the 3' ends of the synthetic probes 110 and 111 other than the nick ends thereof are labeled with digoxigein (DIG). Aside from this, the aforesaid method is followed to produce the DNA fragment 106. At this time, the 3' end of the DNA fragment 106 is labeled with DIG. Thereafter, according to the same method as the aforesaid one, the DNA fragment 106 having the 3' end thereof labeled with DIG is migrated from the first solution vessel 202 to the second solution vessel 203. Since the size of DIG itself is much smaller than the diameter of 1 nm of the nanopore 205, the DNA fragment 106 has therefore the 3' end thereof first introduced into the nanopore 205. When the movement of the DNA fragment 106 is ceased by streptavidin 105, an anti-digoxigenin (DIG) antibody labeled with a bead whose diameter is larger than 1 nm is introduced into the second solution vessel 203, and bound to DIG with which the 3' end of the DNA fragment 106 is labeled. Thereby, an arrayed DNA fragment 115 formed using streptavidin as the first stopper molecule and the bead mediated by a DIG-anti-DIG antibody bond as the second stopper molecule is produced. Herein, an example in which the DIG-anti-DIG bond bead is used as a stopper molecule other than biotin and streptavidin has been described so far. Alternatively, a method of binding a gold particle to a thiolated end of a DNA, a method of modifying an end of a DNA with an amino group, and binding the DNA end to a bead, which is modified with a carboxyl group, through dehydration reaction, or the like may be adopted.

After the arrayed DNA fragment 115 is produced, a voltage is applied from the voltage source 212 so that the electrode 210 can behave as an anode and the electrode 211 can behave as a cathode. This causes the arrayed DNA fragment 115 to migrate from the second solution vessel 203 to the first solution vessel 202 for a certain time. During the migration, a tunneling current is measured using the electrodes 216 and 217 in order to identify base species constituting the arrayed DNA fragment 115. Thereafter, a voltage is applied from the voltage source 212 so that the electrode 210 can behave as the cathode and the electrode 211 can behave as the anode. This causes the arrayed DNA fragment 115 to migrate from the first solution vessel 202 to the second solution vessel 203 for the certain time. During the migration, the tunneling current is measured using the electrodes 216 and 217. By repeating the migration between the solution vessels and the measurement of the tunneling current, the measurement of the tunneling current of the same target DNA molecule can be performed plural times. This permits high-precision determination of base species.

Figure 7:
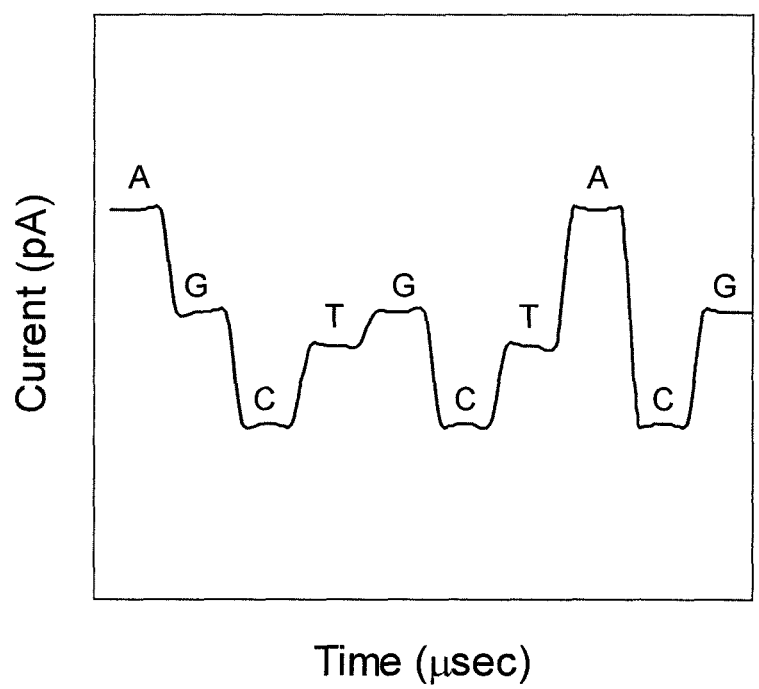
FIG. 7 is a graph of a time-sequential change in a tunneling current value occurring when a DNA molecule passes through a nanopore.

Now, a method for determining base species will be described below. Bases fall into four species of adenine (A), thymine (T), guanine (G), and cytosine (C). An inherent current value is observed for each of the base species, and sent to data processing means 400. FIG. 7 shows an example. In advance, tunneling currents occurring when polymers each of which has bases of one species concatenated pass through a nanopore are measured, and current values associated with the respective base species are obtained and stored in a memory in the data processing means. The data processing means 400 then compares a current value, which is obtained at the time of measuring a tunneling current of a target DNA, with the current values that are associated with the respective base species and that are measured in advance, and thus determines the base species of the target DNA.

As for switching the polarities of a voltage in reciprocation measurement, the voltage source 212 is controlled so that automatic switching can be achieved at intervals of a certain time. A control unit is included in the data processing means 400. The certain time may be variably set. When a stopper molecule approaches a nanopore, a decrease in a current passing through the nanopore can be measured. Therefore, the decrease in the current may be used as a trigger to switch the voltage polarities.

In the present embodiment, measurement of a tunneling current using one nanopore is performed. Alternatively, when plural nanopores are used to concurrently measure tunneling currents of numerous different target DNA molecules, a throughput can be improved.

In the present embodiment, for an explanatory purpose, a description has been made of an example in which after a DNA having a stopper molecule bound to a 5' end thereof is introduced into the first solution vessel and passed through a nanopore, a stopper molecule is bound to a 3' end thereof. In a similar method, a DNA fragment having a stopper molecule bound to a 3' end thereof may be used. After the DNA fragment is introduced into the nanopore, a stopper molecule may be bound to a 5' end thereof.

Embodiment 2

A description will be made of a method for determining a base sequence of a DNA molecule through fluorescence detection measurement which utilizes fluorescence resonance energy transfer (FRET) of a nanopore. A target DNA molecule labeled with a fluorescent substance Cy5 serving as an acceptor is produced according to a method described below. As described in conjunction with FIG. 2B of the embodiment 1, the DNA fragment 106 having the 5' end thereof labeled with biotin-mediated streptavidin and the 3' end thereof labeled with DIG is produced. Thereafter, a reaction solution containing dCTP, dGTP, dTTP, Cy5-labeled dATP, DNA polymerase, and a primer that has a complementary sequence with respect to a synthetic probe portion (either the probe 110 or 111) of the DNA fragment 106, and the DNA fragment 106 having the 3' end thereof labeled with DIG are mixed in order to induce elongation reaction. During the elongation reaction, heat denaturation is not induced. Using different reaction tubes, the same manipulations are performed on a reaction solution in which dCTP alone is labeled with Cy5, a reaction solution in which dGTP alone is labeled, and a reaction solution in which dTTP alone is labeled. Thus, a double-stranded DNA fragment 117 that contains the target DNA fragment 101 and is labeled with a Cy5 fluorescent substance 116 is produced.

Figure 8:
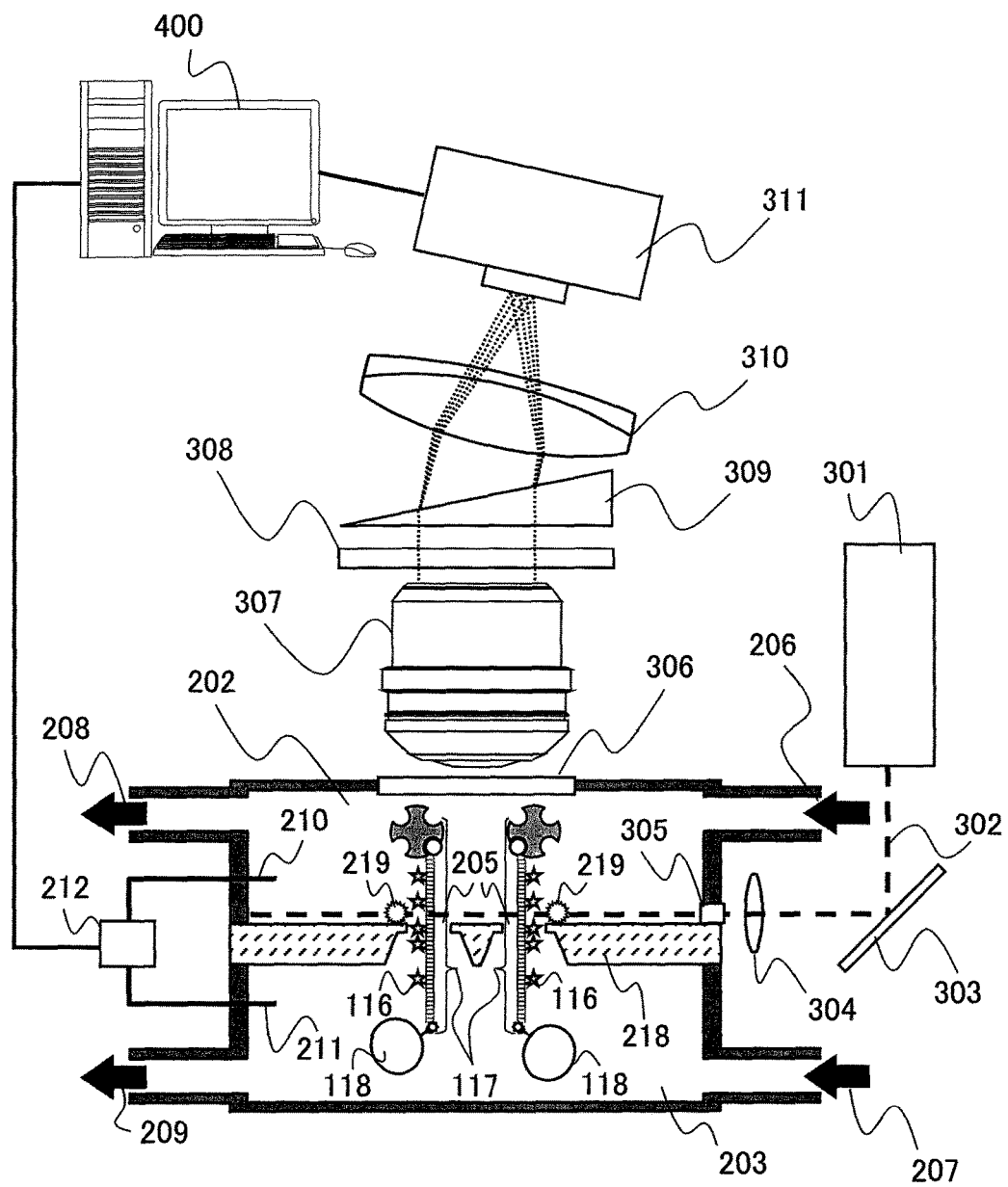
FIG. 8 is a schematic diagram of a nanopore apparatus employed in an embodiment 2.

FIG. 8 is a schematic diagram of a nanopore apparatus employed in the present embodiment. The nanopore apparatus includes a first solution vessel 202, a second solution vessel 203, and a nanopore thin membrane 218 that partitions the solution vessels. The solution vessels 202 and 203 are provided with introduction ports 206 and 207 respectively through which a solution is introduced, and discharge ports 208 and 209 respectively through which the solution is discharged. In order to bring about a voltage gradient between the solution vessels via the nanopore thin membrane 218, the solution vessels 202 and 203 are provided with electrodes 210 and 211 respectively. The electrodes 210 and 211 are connected to a voltage source 212 capable of changing polarities. The first solution vessel 202 has an optically transparent irradiation window 305 and a detection window 306. The nanopore thin membrane 218 is formed with a $Si_3N_4$ thin membrane having nanopores 205 of 3 nm in diameter formed therein. The plural nanopores 205 are formed like a grid at intervals of 1 μm. In the vicinity of the nanopores 205, Qdots (605) 219 that is excited with blue light and emits fluorescent light of 605 nm are immobilized as donors.

Figure 9:
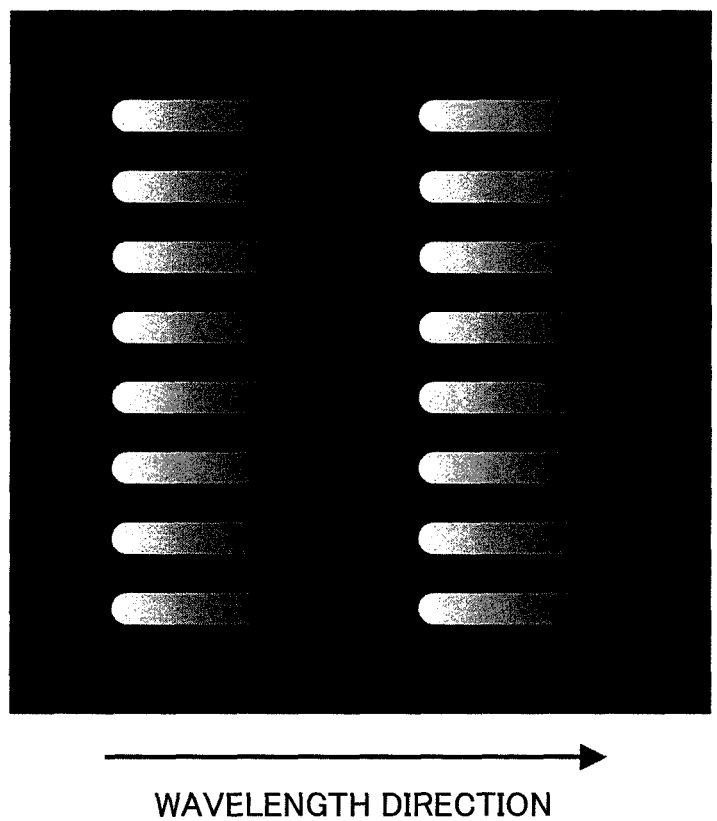
FIG. 9 is a diagram of an image on a CCD of light emitted through each nanopore in the embodiment 2.

Laser light 302 oscillated by a laser light source (wavelength of 488 nm) 301 has the angle thereof adjusted by a mirror 303, concentrated by a condenser lens 304, and irradiated to all the Qdots 219 through the irradiation window 305. Fluorescent light emitted near each of the nanopores 205 is concentrated by an objective lens 307 through the detection window 306, has light other than light, which has a wavelength ranging from 550 nm to 700 nm, cut by a filter 308, and is spectroscopically diffracted by a prism 309. An image is, as shown in FIG. 9, formed on a CCD 311 by an image formation lens 310. Data of the CCD 311 is stored in the data processing means 400. FIG. 9 shows the image formed on the CCD 311 and stored in the data processing means 400. Spots represent luminescent points of the respective nanopores. The axis of abscissas is associated with a wavelength direction.

The double-stranded DNA fragment 117 obtained according to the foregoing method is mixed in a buffer solution and introduced into the first solution vessel 202 through the introduction port 206. The buffer solution alone is introduced into the second solution vessel 203 through the introduction port 207. A voltage is applied from the voltage source 212 so that the electrode 210 can behave as a cathode and the electrode 211 can behave as an anode. This causes the double-stranded DNA fragment 117 to migrate from the first solution vessel 202 to the second solution vessel 203. Since the size of streptavidin 105 is on the order of 5 nm, the streptavidin 105 cannot pass through the nanopore of 3 nm in diameter. The double-stranded DNA fragment 117 has an end thereof, which is not labeled with the streptavidin 105, first introduced into the nanopore 205. With the movement of the double-stranded DNA fragment 117 ceased by the streptavidin 105, an anti-DIG antibody 118 labeled with a bead whose diameter is larger than 3 nm is introduced into the second solution vessel 203. The anti-DIG antibody 118 is bound to DIG with which the 3' end of the double-stranded DNA fragment 117 which is not labeled with the fluorescent substance 116 is labeled. After labeling with the anti-DIG antibody 118 is completed, the buffer alone is introduced through the introduction port 207 in order to remove an anti-DIG antibody, which has not reacted, from the second solution vessel 203. Meanwhile, the voltage is kept applied. Incidentally, a target DNA molecule included in the double-stranded DNA fragment 117 introduced into each of the nanopores may be the same one or may be a DNA molecule different from the others. By statistically processing detected light waves, respective base species can be identified. When one and the same DNA molecule is employed, a time can be shortened by decreasing the reciprocating frequency of the DNA molecule, and precision in identifying base species can be improved. In contrast, when different molecules are employed, many molecules can be concurrently measured and a throughput can be improved.

Figure 10:
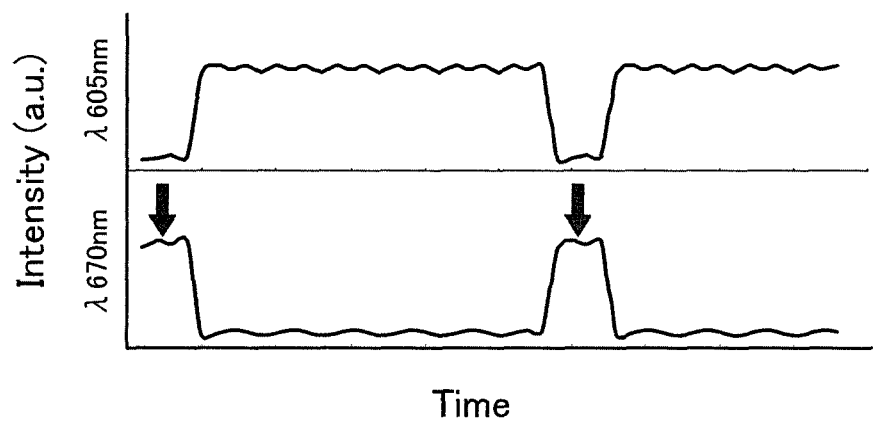
FIG. 10 includes graphs of time-sequential changes in a signal intensity at respective wavelengths occurring when a DNA molecule passes through a nanopore.
Figure 11:
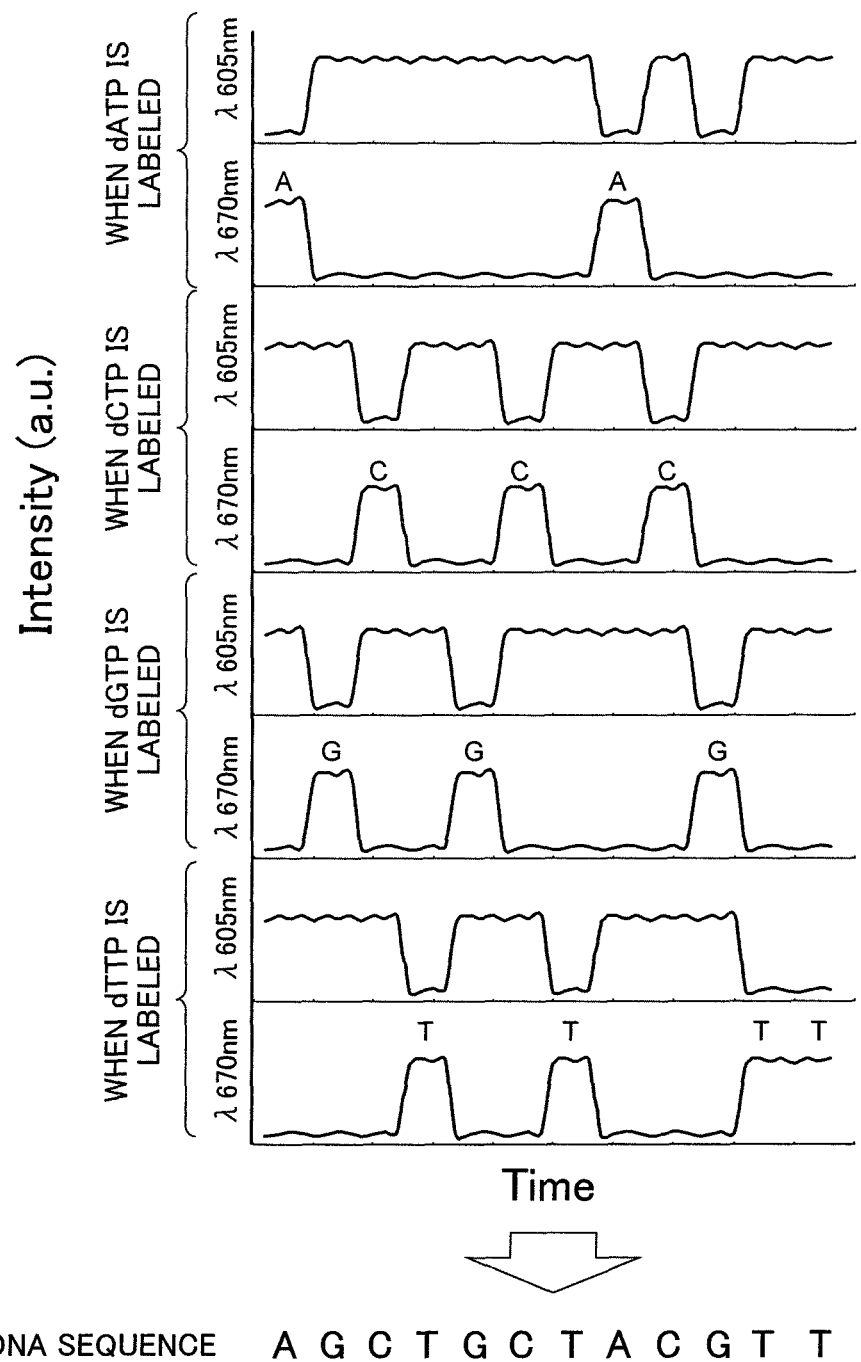
FIG. 11 includes graphs of time-sequential changes in a signal intensity relative to respective base species occurring when the DNA molecule passes through the nanopore.

After the double-stranded DNA fragment 117 is labeled with the anti-DIG antibody 118, the laser light 302 is oscillated from the laser light source 301 in order to excite the Qdots 219. Thereafter, a voltage is applied from the voltage source 212 so that the electrode 210 can behave as an anode and the electrode 211 can behave as a cathode. This causes the anti-DIG antibody 118-labeled double-stranded DNA fragment 117 to migrate from the second solution vessel 203 to the first solution vessel 202 for a certain time. During the migration, when the fluorescent substance 116 with which the double-stranded DNA fragment 117 is labeled passes near the Qdot 219, transfer of excitation energy due to resonance takes place and causes the fluorescent substance 116 to emit light. The emitted light is detected by the CCD 311. FIG. 10 shows temporal variations in the intensities of pixels, which are associated with the wavelengths of 605 nm and 670 nm respectively, in the spots on the CCD 311 representing the emitted light waves. The wavelength of 605 nm corresponds to light emitted from the Qdot 219, while the wavelength of 670 nm corresponds to light emitted from the fluorescent substance 116. Based on the detected temporal variation in a signal intensity associated with the wavelength of 670 nm, the position of labeling of the double-stranded DNA fragment 117 with the fluorescent substance 118 can be calculated. Thereafter, a voltage is applied from the voltage source 212 so that the electrode 210 can behave as the cathode and the electrode 211 can behave as the anode. This causes the double-stranded DNA fragment 117 to migrate from the first solution vessel 202 to the second solution vessel 203 for the certain time. During the migration, fluorescent light is, as mentioned above, detected by the CCD 311. By repeating the migration and the detection of the fluorescent light, the position of labeling of the double-stranded DNA fragment 117 with the fluorescent substance 116 can be measured plural times. The position can therefore be highly precisely calculated. FIG. 11 shows temporal variations in signal intensities obtained at respective wavelengths after performing repetitive work of migration and detection of fluorescent light similar to the foregoing ones on the double-stranded DNA fragment 117 having four different kinds of dNTPs thereof labeled with a fluorescent substance. Based on the temporal variation in the signal intensity associated with the wavelength of 670 nm, the position of each base species in the target DNA molecule 101 can be distinguished. By combining data items of respective base species, the base sequence of the target DNA molecule 101 is determined.

For the switching of voltage polarities in reciprocation measurement, the voltage source 212 is controlled so that automatic switching can be achieved at intervals of a certain time. The certain time can be variably set. A control unit is incorporated in the data processing means 400. When a stopper molecule approaches a nanopore, a decrease in a current passing through the nanopore is measured. Therefore, the voltage polarities may be switched with the decrease in the current as a trigger.

In the present embodiment, only one kind of fluorescent substance is employed. Alternatively, four kinds of dNTPs may be labeled with different fluorescent substances, and a double-stranded DNA fragment 117 having all the dNTPs thereof labeled may be produced, and fluorescent light may be detected by performing the same manipulations as the aforesaid ones. Thus, the base sequence of the target DNA molecule 101 may be determined. By using a high-viscosity buffer solution or decreasing a voltage to be applied for migration, the migration speed of the double-stranded DNA fragment 117 can be lowered, and fluorescent light can be highly sensitively detected. In the present embodiment, Qdots are adopted as donors for FRET. Alternatively, a fluorescent substance will do. In addition, although FIG. 8 shows an example in which two DNA fragments are concurrently measured, one DNA fragment may be measured or three or more DNA fragments may be concurrently measured.

Embodiment 3

Figure 12:
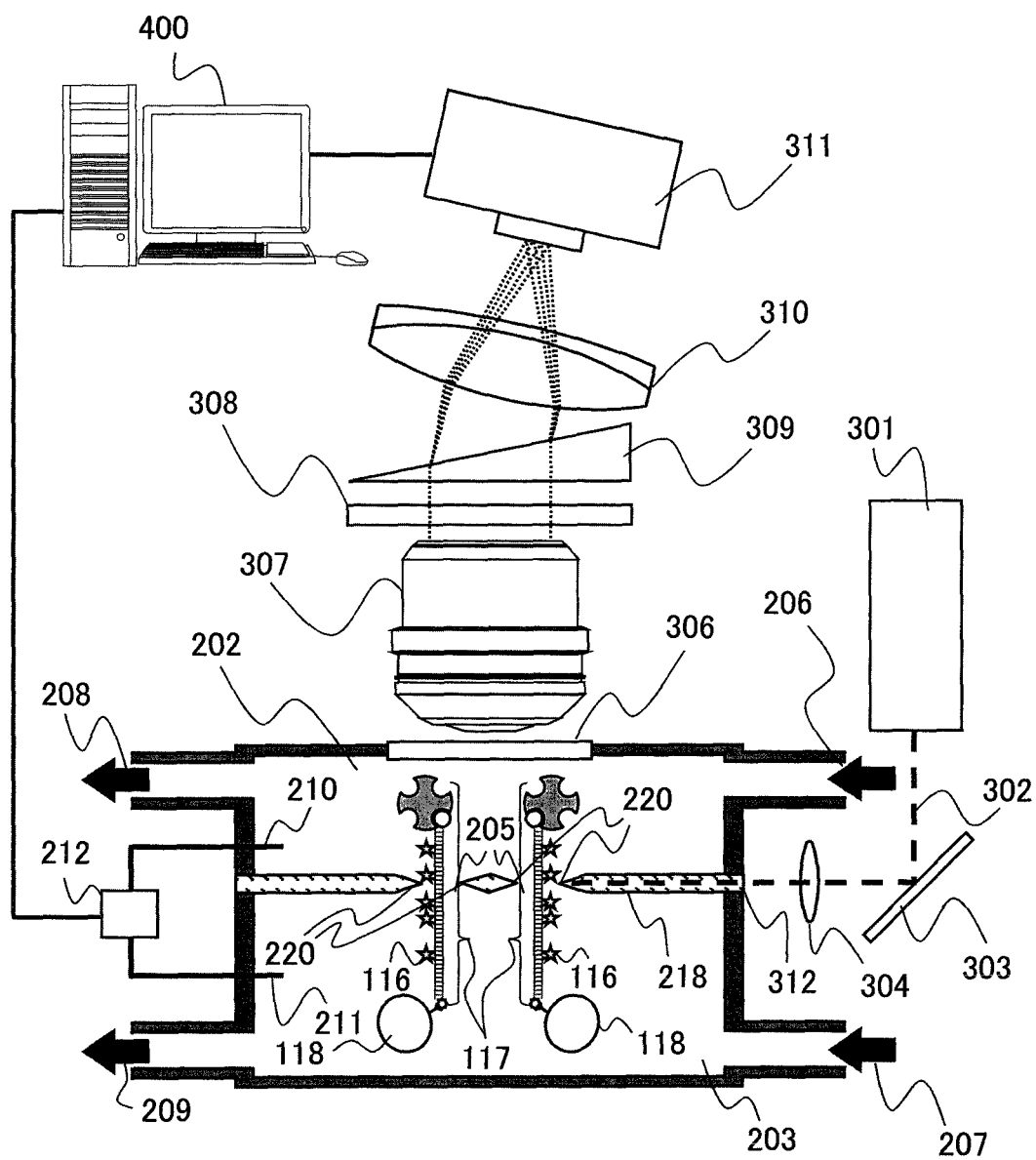
FIG. 12 is a schematic diagram of a nanopore apparatus employed in an embodiment 3.

A description will be made of a method for determining a base sequence of a DNA molecule through detection and measurement of fluorescent light through a nanopore. FIG. 12 is a schematic diagram of a nanopore apparatus employed in the present embodiment. Constituent features other than a laser light source 301, a filter 308, a position of irradiation of laser light to the nanopore apparatus, and the construction of a nanopore thin membrane are identical to those of the embodiment 2. A nanopore thin membrane 218 is made of quartz glass, and the surface of the nanopore thin membrane 218 is coated with a resin whose refractive index is lower than that of quartz (for example, Fluorinert). At this time, a resin is peeled off from sharp distal ends 220 near nanopores. Laser light 302 emitted from a laser light source (wavelength of 633 nm) 301 is concentrated by a condenser lens 304 and irradiated to the flank 312 of the nanopore thin membrane. At this time, the laser light 302 propagates through the nanopore thin membrane 218 while totally reflecting. However, since the distal ends 220 are not resin-coated, the laser light slightly oozes as near-field light to a buffer solution with which the solution vessels are filled. Since the laser light 302 propagates through the entire nanopore thin membrane 218 while totally reflecting, a near field occurs at each of the distal ends 220. Fluorescent light emitted near each of nanopores 205 is concentrated by an objective lens 307 via a detection window 306. Light other than light whose wavelength ranges from 660 nm to 700 nm is cut by a filter 308, and the remaining light is spectroscopically diffracted by a prism 309. An image is then formed on a CCD 311 by an image formation lens 310. Data of the CCD 311 is stored in data processing means 400. FIG. 12 shows an example in which two DNA fragments are concurrently measured. Alternatively, one DNA fragment may be measured or three or more DNA fragment may be concurrently measured.

According to the same method as the one in the embodiment 2, manipulations are performed for producing a double-stranded DNA fragment 117, and binding an anti-DIG antibody 118, which is labeled with a bead whose diameter is larger than 3 nm, to DIG with which a 3' end of a strand that is not labeled with a fluorescent substance 116.

After the double-stranded DNA fragment 117 is labeled with the anti-DIG antibody 118, laser light 302 is oscillated from the laser light source 301 in order to produce near-field light at each of the distal ends 220. Thereafter, a voltage is applied from a voltage source 212 so that an electrode 210 can behave as an anode and an electrode 211 can behave as a cathode. This causes the anti-DIG antibody 118-labeled double-stranded DNA fragment 117 to migrate from the second solution vessel 203 to the first solution vessel 202 for a certain time. During the migration, when a fluorescent substance 116 with which the double-stranded DNA fragment 117 is labeled passes through the near-field light in the vicinity of each of the distal ends 220, the fluorescent substance 116 emits light. The emitted light is detected by a CCD 311. Based on a temporal variation in a detected signal intensity, a position of labeling of the double-stranded DNA fragment 117 with the fluorescent substance 116 can be calculated. Thereafter, a voltage is applied from the voltage source 212 so that the electrode 210 can behave as the cathode and the electrode 211 can behave as the anode. This causes the double-stranded DNA fragment 117 to migrate from the first solution vessel 202 to the second solution vessel 203 for the certain time. During the migration, the emitted light is detected by the CCD 311. By repeating the migration and the detection of emitted light, the position of labeling of the double-stranded DNA fragment 117 with the fluorescent substance 116 can be measured plural times. This permits high-precision position calculation. Manipulations for detecting a fluorescent-substance labeled position are performed on the double-stranded DNA fragment 117, which has four different kinds of dNTPs thereof labeled with a fluorescent substance, in order to determine the base sequence of the target DNA molecule 101.

For switching of voltage polarities in reciprocation measurement, the voltage source 212 is controlled so that automatic switching can be achieved at intervals of a certain time. The certain time can be variably set. A control unit may be incorporated in the data processing means 400. When a stopper molecule approaches a nanopore, a decrease in a current passing through the nanopore can be measured. Therefore, the switching of the voltage polarities may be performed with the decrease in the current as a trigger.

In the present embodiment, only one kind of fluorescent substance is used. Alternatively, four kinds of dNTPs may be labeled with different fluorescent substances. The double-stranded DNA fragment 117 having all the dNTPs thereof labeled may be produced, and fluorescent light may be detected by performing the same manipulations as the foregoing ones. Thus, the base sequence of the target DNA molecule 101 may be determined. In addition, by using a high-viscosity buffer solution or decreasing a voltage to be applied during migration, the migration speed of the double-stranded DNA fragment 117 can be lowered. Eventually, the fluorescence light can be detected highly sensitively.

Embodiment 4

A description will be made of a method for determining a base sequence of a DNA molecule on a hybridization basis. A DNA fragment 106 containing a target DNA molecule 101 that has streptavidin bound to a 5' end thereof is produced according to the same method as the one in the embodiment 1.

Figure 13:
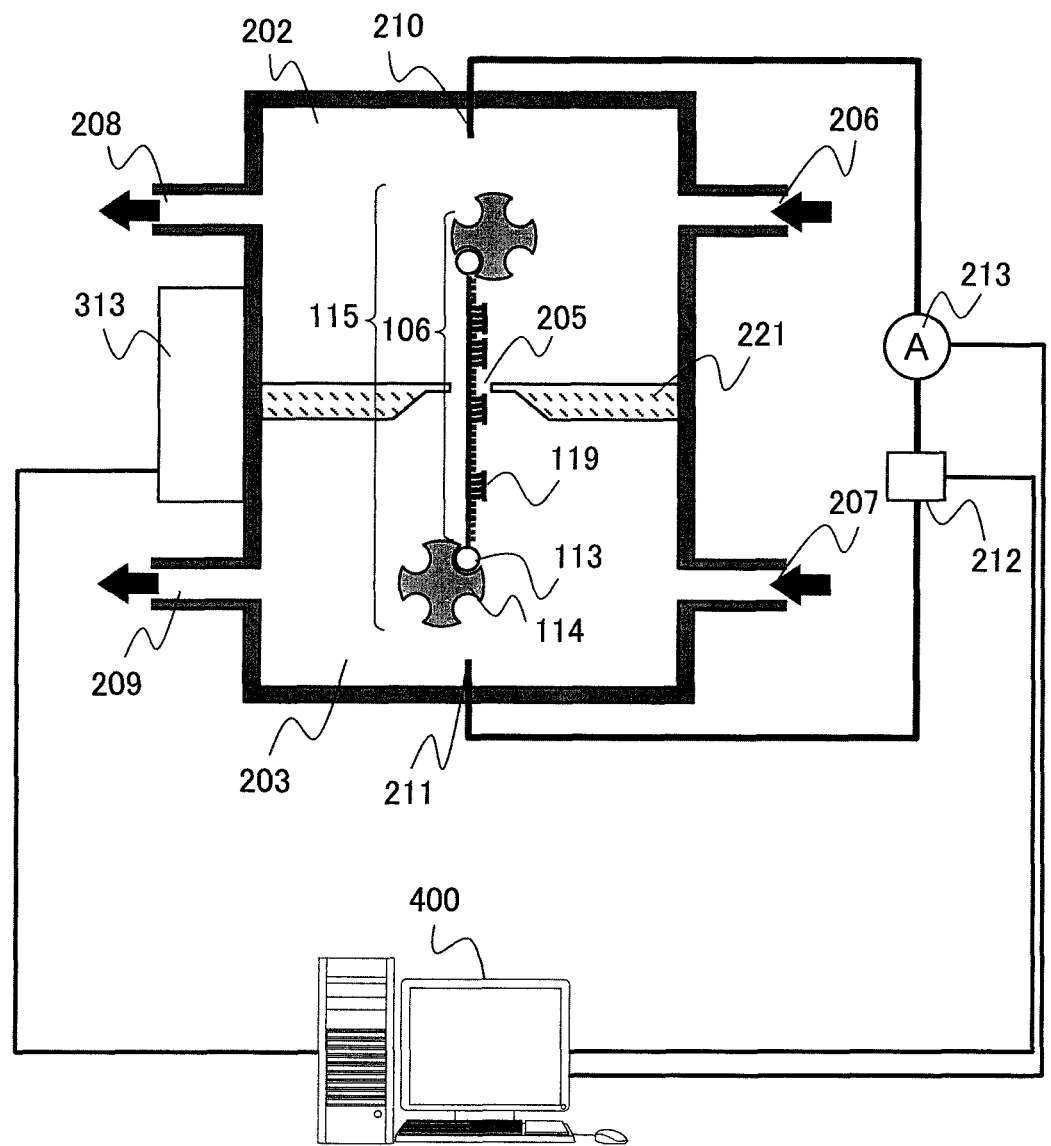
FIG. 13 is a schematic diagram of a nanopore apparatus employed in an embodiment 4.

FIG. 13 shows a schematic diagram of a nanopore apparatus employed in the present embodiment. The nanopore apparatus includes a first solution vessel 202, a second solution vessel 203, and a nanopore thin membrane 221 that partitions the solution vessels. The solution vessels are provided with introduction ports 206 and 207 respectively through which a solution is introduced, and discharge ports 208 and 209 respectively through which the solution is discharged. In order to bring about a voltage gradient between the solution vessels via the nanopore thin membrane 221, the solution vessels are provided with electrodes 210 and 211 respectively. The electrodes 210 and 211 are connected to a voltage source 212 capable of changing polarities and an ammeter 213. The nanopore thin membrane 221 is constructed with a $Si_3N_4$ thin membrane in which a nanopore 205 of 3 nm in diameter is formed. Using a temperature adjustment unit 313, the temperature of the solution in the first solution vessel 202 and second solution vessel 203 can be adjusted to range from 20° C. to 100° C. Control of the voltage source 212, control of the temperature adjustment unit 313, acquisition of a current value of the ammeter 213, and processing of obtained data are carried out by data processing means 400.

The DNA fragment 106 obtained according to the aforesaid method is mixed in a buffer solution and introduced into the first solution vessel 202 through the introduction port 206. The buffer solution alone is introduced into the second solution vessel 203 through the introduction port 207. A voltage is applied from the voltage source 212 so that the electrode 210 can behave as a cathode and the electrode 211 can behave as an anode. This allows the DNA fragment 106 to migrate from the first solution vessel 202 to the second solution vessel 203. Concurrently with the voltage application, a current is measured using the ammeter 213. Since the size of streptavidin 105 is on the order of 5 nm, the streptavidin cannot pass through the nanopore of 3 nm in diameter. The DNA fragment 106 has the 3' end thereof (end that is not labeled with the streptavidin 105) first introduced into the nanopore 205. When the DNA fragment 106 is introduced into the nanopore 205, a current value decreases. As mentioned previously, the size of the streptavidin 105 is larger than the diameter of the nanopore 205. Therefore, immediately before the streptavidin 105 passes through the nanopore 205, the movement of the DNA fragment 106 to the second solution vessel 203 is ceased. After the decrease in the current is verified, a biotin-3' end-DNA labeling kit is inserted into the second solution vessel 203 through the introduction port 207 in order to label the 3' end of the DNA fragment 106 with biotin 113. After labeling with biotin is completed, the buffer alone is introduced through the introduction port 207 in order to remove biotin, which has not reacted, from the second solution vessel 203. A solution containing streptavidin is introduced through the introduction port 207 in order to bind the streptavidin 114 to the biotin 113, with which the 3' end of the DNA fragment 106 is labeled, whereby an arrayed DNA fragment 115 is produced. The buffer alone is introduced through the introduction port 207 in order to remove streptavidin, which has not reacted, from the second solution vessel 203.

After the arrayed DNA fragment 115 is produced, a known-sequence probe 119 including six bases is introduced into the solution vessels through the introduction ports 206 and 207 respectively, and hybridized to the arrayed DNA fragment 115. After hybridization reaction is completed, a buffer alone is introduced through the introduction ports 206 and 207 in order to remove the known-sequence probe 119, which has not reacted, from the solution vessels 203. A voltage is applied from the voltage source 212 so that the electrode 210 can behave as the anode and the electrode 211 can behave as the cathode. This allows the arrayed DNA fragment 115 to migrate from the second solution vessel 203 to the first solution vessel 202 for a certain time. Thereafter, a voltage is applied from the voltage source 212 so that the electrode 210 can behave as the anode and the electrode 211 can behave as the cathode. This allows the arrayed DNA fragment 115 to migrate from the first solution vessel 202 to the second solution vessel 203 for the certain time. As for the timing of switching the voltage polarities, the voltage source 212 is controlled so that automatic switching can be achieved at intervals of the certain time. The certain time can be variably set. When a stopper molecule approaches the nanopore, a decrease in a current passing through the nanopore can be measured. Therefore, the switching of the voltage polarities may be performed with the decrease in the current as a trigger. During the migration of the arrayed DNA fragment 115, the ammeter 213 is used to measure a blockage current. Based on a temporal variation in the measured blockage current, a position at which the known-sequence probe 119 is hybridized to the arrayed DNA fragment 115 can be calculated.

Thereafter, voltage application is ceased. The temperature adjustment unit 313 is used to raise the temperature of the solution in the first solution vessel 202 and second solution vessel 203 up to 95° C. for a certain time. The known-sequence probe 119 is separated from the arrayed DNA fragment 115 through heat denaturation. A buffer alone is introduced through the introduction ports 206 and 207 in order to remove the known-sequence probe 119 from the solution vessels. The temperatures of the solution vessels are lowered to 40° C. A known-sequence probe having a different sequence from the known-sequence probe 119 is introduced into the solution vessels through the introduction ports 206 and 207 respectively, and hybridized to the arrayed DNA fragment 115. After the hybridization reaction is completed, the buffer alone is introduced through the introduction ports 206 and 207 in order to remove the known-sequence probe, which has not reacted, from the solution vessels. A voltage is applied from the voltage source 212 so that the electrode 210 can behave as the anode and the electrode 211 can behave as the cathode. This causes the arrayed DNA fragment 115 to migrate from the second solution vessel 203 to the first solution vessel 202 for a certain time. Thereafter, a voltage is applied from the voltage source 212 so that the electrode 210 can behave as the cathode and the electrode 211 can behave as the anode. This causes the arrayed DNA fragment 115 to migrate from the first solution vessel 202 to the second solution vessel 203 for the certain time. During the migration, the ammeter 213 is used to measure a blockage current.

Figure 14:
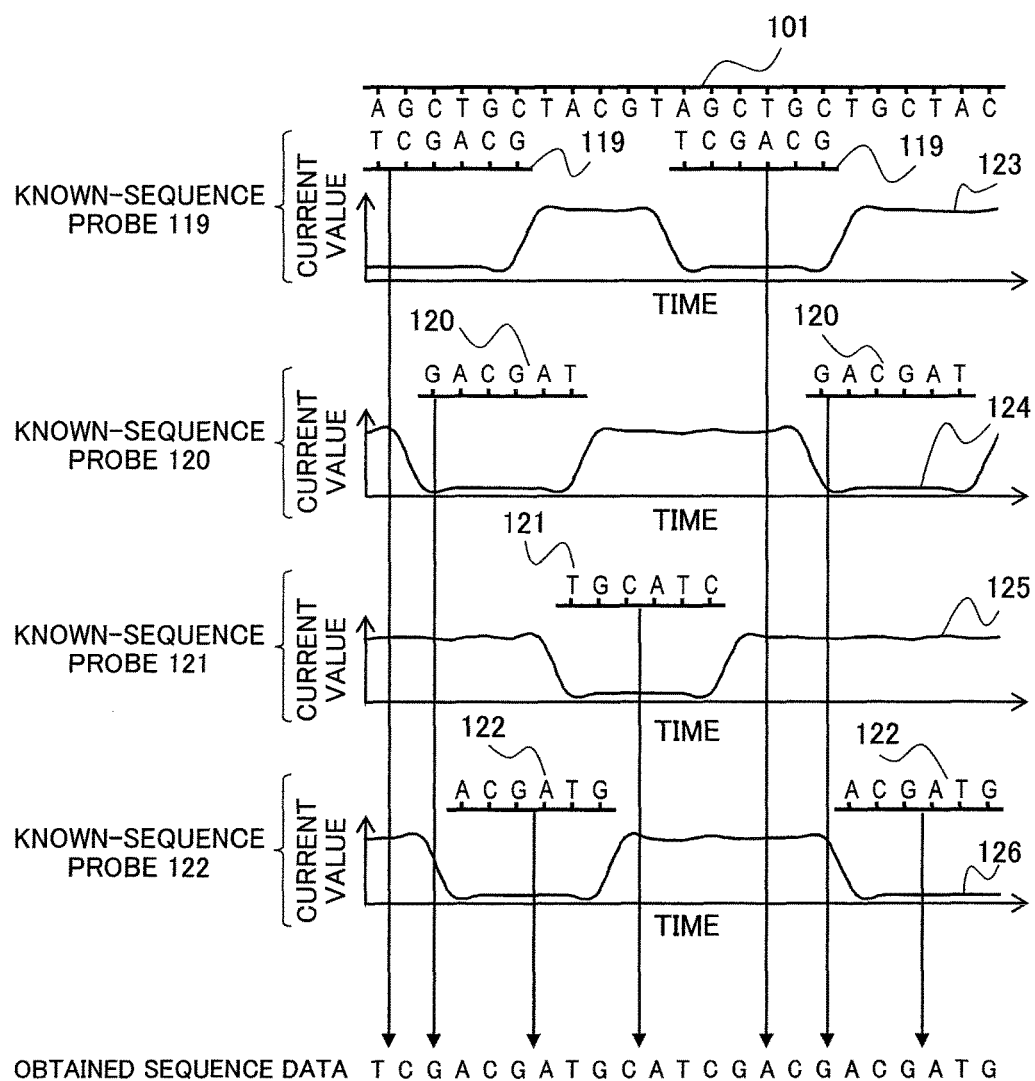
FIG. 14 includes graphs of time-sequential changes in a blockage current occurring when a DNA molecule to which respective known-sequence probes are hybridized passes through a nanopore.

Hybridization of a known-sequence probe to an arrayed DNA fragment, migration of the arrayed DNA fragment, measurement of a blockage current, and separation of the known-sequence probe from the arrayed DNA fragment through heat denaturation are repeated $4^n$ times (where n denotes the base length of the known-sequence probe, that is, 6 in the present embodiment) using known-sequence probes having different sequences. Data items of the positions of hybridization of the respective known-sequence probes can be converted into the base sequence data of the target DNA molecule 101 using a computer algorithm. A concrete method will be described below in conjunction with FIG. 14. After the known-sequence probe 119 is hybridized to the target DNA 101, and passed through a nanopore, when a blockage current is measured, a waveform 123 of block current values is observed. The measurement is repeated according to the method described previously in order to estimate to what position in the target DNA 101 the known-sequence probe 119 is hybridized. The foregoing manipulations are performed using known-sequence probes 120, 121, and 120. The obtained positions of hybridization of the respective known-sequence probes to the target DNA 101 are superposed on one another, whereby a sequence complementary to that of the target DNA 101 can be drawn out. Eventually, sequence data of the target DNA 101 can be obtained.

By utilizing the present invention, determination of a base sequence of a target DNA molecule on a hybridization basis can be achieved without amplification of the target DNA molecule and without use of plural nanopores.

In the present embodiment, the length of a known-sequence probe is six bases. If the length of the known-sequence probe is long, a rise in a cost of probe production or an increase in erroneous hybridization takes place. In contrast, if the length of the known-sequence probe is short, unless a measurement resolution is raised, an accurate position of hybridization of a probe cannot be measured. Therefore, the length of the known-sequence probe preferably ranges from about three bases to about ten bases.

In order to highly precisely detect a position of hybridization of a known-sequence probe to a target DNA molecule, when a blockage current is measured, the polarities of the electrodes 210 and 211 may be repeatedly changed in order to measure the blockage current plural times.

After measurement is completed, a nuclease or an acid may be used to cut the arrayed DNA fragment 115 so as to remove the arrayed DNA fragment 115 from the solution vessels. Thus, a nanopore thin membrane may be reused.

For detection of a position of hybridization of a known-sequence probe, part of the known-sequence probe may be labeled with a fluorescent substance, and fluorescent-light detection described in relation to the embodiment 2 or 3 may be employed.

For detection of a position of hybridization of a known-sequence probe, if a tunneling current or fluorescent light is detected instead of a blockage current, concurrent measurement of plural target molecules can be readily achieved. Eventually, a throughput can be improved.

INDUSTRIAL APPLICABILITY

DNA sequencer

REFERENCE SIGNS LIST

101: target DNA molecule, 102: biotin, 103: synthetic probe, 104: end face, 105: streptavidin, 106: DNA fragment, 107: vector, 108: restriction site, 109: restriction site, 110: synthetic probe, 111: synthetic probe, 112: fragment, 113: biotin, 114: streptavidin, 115: arrayed DNA fragment, 116: fluorescent substance, 117: double-stranded DNA fragment, 118: bead-labeled anti-DIG antibody, 119: known-sequence probe, 120: known-sequence probe, 121: known-sequence probe, 122: known-sequence probe, 123: waveform of blockage current values, 124: waveform of blockage current values, 125: waveform of blockage current values, 126: waveform of blockage current values, 202: first solution vessel, 203: second solution vessel, 204: nanopore thin membrane, 205: nanopore, 206: introduction port, 207: introduction port, 208: discharge port, 209: discharge port, 210: electrode, 211: electrode, 212: voltage source, 213: ammeter, 214: ammeter, 215: voltage source, 216: electrode, 217: electrode, 218: nanopore thin membrane, 219: Qdot, 220: distal end, 221: nanopore thin membrane, 301: laser light source, 302: laser light, 303: mirror, 304: condenser lens, 305: irradiation window, 306: detection window, 307: objective lens, 308: filter, 309: prism, 310: image formation lens, 311: CCD, 312: flank of a nanopore thin film, 313: temperature adjustment unit, 400: data processing unit

The invention claimed is:

1. A system for determining an alignment of monomers constituting a biopolymer, wherein the system comprises:
    a first solution vessel and a second solution vessel partitioned by a membrane;
    a pair of electrodes configured to move the biopolymer between the first solution vessel and the second solution vessel through the nanopore, wherein the pair of electrodes in the first solution vessel and the second solution vessel is connected to a voltage source configured to bring about a voltage gradient by the electrodes between the first solution vessel and the second solution vessel;
    a first introduction port configured to introduce the biopolymer, which has a first stopper molecule bound to one end of the biopolymer that is an object of measurement, into the first solution vessel, wherein the first stopper molecule is larger than a diameter of the nanopore;
    a second introduction port configured to introduce a second stopper molecule, which is bound to the other end of the biopolymer having passed through the nanopore, into the second solution vessel, wherein the second stopper molecule is larger than a diameter of the nanopore;
    an ammeter operatively connected to the pair of electrodes, wherein the ammeter detects a signal generated along with the movement of the biopolymer made by the pair of electrodes; and
    a data processor programmed to:
        apply a voltage gradient between the pair of electrodes to cause the biopolymer to migrate from the second solution vessel to the first solution vessel for a first interval of time;
        automatically switch polarity of the pair of electrodes when the ammeter measures a decrease in current passing though the nanopore that is caused by approach of the first or second stopper molecule to the nanopore;
        apply a voltage gradient between the pair of electrodes to cause the biopolymer to migrate from the first solution vessel to the second solution vessel for a second interval of time;
        measure a temporal change in the signal detected by the ammeter;
        calculate the signal as data dependent on species of monomers constituting the biopolymer; and
        determine the alignment of the monomers constituting the biopolymer.

2. The system of claim 1, wherein the biopolymer has a specific monomer thereof labeled with a fluorescent substance and wherein the system further comprises:
    a light source configured to irradiate light to the biopolymer which passes through the nanopore; and
    a charge-coupled device (CCD), wherein the charge-coupled device detects light emitted due to the irradiation of light.

3. The system of claim 1, further comprising:
    a set of known-sequence probes, wherein the biopolymer is a single-stranded nucleic acid; and
    a third introduction port, wherein the third induction port introduces the known-sequence probe into at least one of the first and second solution vessels; and
    wherein the data processor is further programmed to measure a temporal change in a signal of presence or absence of the known-sequence probe, which is bound to the single-stranded nucleic acid, along with the movement of the single-stranded nucleic acid.

4. The system of claim 1, wherein at least one of the first and second stopper molecules is streptavidin.

5. The system of claim 4, wherein at least one of the first and second stopper molecules is a bead to be bound to the biopolymer by a DIG-anti-DIG antibody bond.

6. The system of claim 1, wherein the data processor is further programmed to calculate, for each interval of time, a position of the monomers on the biopolymer, and determine the alignment of the monomers constituting the biopolymer based on the calculated positions of the monomers.

7. The system of claim 1, wherein the data processor is further programmed to repeat switching the polarity of the pair of electrodes and apply a voltage gradient between the pair of electrodes to cause the biopolymer to migrate between the first solution vessel and the second solution vessel.

8. The system of claim 1, wherein the first interval of time is different from the second interval of time.

9. A system, comprising:
    a first solution vessel having an introduction port, wherein the introduction port introduces a biopolymer and a first stopper molecule, wherein the first stopper molecule is bound to one end of the biopolymer;
    a second solution vessel having an introduction port configured to introduce a second stopper molecule, wherein the second stopper molecule is bound to another end of the biopolymer;

a membrane partitioning the first and second solution vessels, the membrane having a nanopore configured to be large enough to allow portions of biopolymer between the ends to pass therethrough and smaller than the first and second stopper molecules to hinder the first and second stopper molecules from passing therethrough, the membrane formed with an insulator membrane comprising at least one of $Si_3N_4$, a plastic material, or a metallic material, and the insulator membrane comprising the nanopore of between approximately 0.5 nm and approximately 50 nm in diameter formed therein;

a pair of electrodes operatively connected to a voltage source, the electrodes having ends provided in the first and second solution vessels, and wherein the pair of electrodes bring about a voltage gradient between the first and second solution vessels to move portions of biopolymer between the ends between the first solution vessel and second solution vessel through the nanopore in the membrane;

an ammeter, wherein the ammeter detects a signal generated along with the movement of the biopolymer made by the pair of electrodes, including detecting a current passing through the nanopore;

a data processor programmed to:
  apply a voltage gradient between the pair of electrodes to cause the biopolymer to migrate from the second solution vessel to the first solution vessel for a first interval of time;
  automatically switch polarity of the pair of electrodes when the ammeter measures a decrease in current passing though the nanopore that is caused by approach of the first or second stopper molecule to the nanopore;
  apply a voltage gradient between the pair of electrodes to cause the biopolymer to migrate from the first solution vessel to the second solution vessel for a second interval of time;
  measure a temporal change in the signal detected by the ammeter;
  calculate the signal as data dependent on species of monomers constituting the biopolymer; and
  determine the alignment of the monomers constituting the biopolymer.

10. The system of claim 9, wherein at least one of the first and second stopper molecules is streptavidin.

11. The system of claim 9, wherein at least one of the first and second stopper molecules is a bead to be bound to the biopolymer by a DIG-anti-DIG antibody bond.

12. The system of claim 9, wherein the biopolymer has a specific monomer thereof labeled with a fluorescent substance, and wherein the system further comprises:
  a light source, wherein the light source irradiates light to the biopolymer which passes through the nanopore, and wherein the detector detects light emitted due to the irradiation of light.

13. A system, comprising:
  a first solution vessel having an introduction port configured to introduce a biopolymer and a first stopper molecule, wherein the first stopper molecule is bound to one end of the biopolymer;
  a second solution vessel having an introduction port configured to introduce a second stopper molecule, wherein the second stopper molecule is bound to another end of the biopolymer;
  a membrane partitioning the first and second solution vessels, the membrane having a nanopore configured to be large enough to allow portions of biopolymer between the ends to pass therethrough and smaller than the first and second stopper molecules to hinder the first and second stopper molecules from passing therethrough, the membrane formed with an insulator membrane comprising at least one of $Si_3N_4$, a plastic material, or a metallic material, and the insulator membrane comprising the nanopore of between approximately 0.5 nm and approximately 50 nm in diameter formed therein;
  a pair of electrodes operatively connected to a voltage source and an ammeter, the electrodes having ends provided in the first and second solution vessels, and wherein the pair of electrodes bring about a voltage gradient between the first and second solution vessels to move portions of biopolymer between the ends between the first solution vessel and second solution vessel through the nanopore in the membrane;
  wherein the biopolymer has a specific monomer thereof labeled with a fluorescent substance, and the system further comprises a light source, wherein the light source irradiates light to the biopolymer which passes through the nanopore;
  a charge-coupled device (CCD), wherein the charge-coupled device detects an emitted light generated by the movement of the biopolymer; and
  a data processor programmed to:
    apply a voltage gradient between the pair of electrodes to cause the biopolymer to migrate from the second solution vessel to the first solution vessel for a first interval of time;
    automatically switch polarity of the pair of electrodes when the ammeter measures a decrease in current passing though the nanopore that is caused by approach of the first or second stopper molecule to the nanopore;
    apply a voltage gradient between the pair of electrodes to cause the biopolymer to migrate from the first solution vessel to the second solution vessel for a second interval of time;
    measure a temporal change in the intensities of pixels captured in the emitted light detected by the CCD; and
    determine the alignment of the monomers constituting the biopolymer based on the measured temporal change.

* * * * *